United States Patent [19]

Kato et al.

[11] 4,339,536

[45] Jul. 13, 1982

[54] PROCESS FOR THE PREPARATION OF LONG-CHAIN DICARBOXYLIC ACIDS BY FERMENTATION

[75] Inventors: Koichi Kato, Hohya; Namio Uemura, Oga, both of Japan

[73] Assignee: Nippon Mining Co., Ltd., Tokyo, Japan

[21] Appl. No.: 156,117

[22] Filed: Jun. 3, 1980

[30] Foreign Application Priority Data

Jun. 8, 1979 [JP] Japan .................................. 54-72089
Jul. 5, 1979 [JP] Japan .................................. 54-85330

[51] Int. Cl.$^3$ ............................................... C12P 7/44
[52] U.S. Cl. .................................... 435/142; 435/176; 435/924
[58] Field of Search .............. 435/924, 142, 249, 255, 435/261, 812, 176

[56] References Cited

U.S. PATENT DOCUMENTS 3,843,466 10/1974 Akabori et al. ...................... 435/142
3,878,093 4/1975 Kanani et al. ....................... 435/261
4,081,367 3/1978 Hulls et al. .......................... 435/255
4,248,971 2/1981 Yousset .............................. 435/255

FOREIGN PATENT DOCUMENTS 45-16750 12/1970 Japan .
50-58284 5/1975 Japan .
1421155 1/1976 United Kingdom ................ 435/924

OTHER PUBLICATIONS

Kirk-Othmer Encyclopedia of Chemical Technology, Third Ed., v. 7, pp. 611, 612, Wiley, N.Y., 1978.

Primary Examiner—Hiram Bernstein
Attorney, Agent, or Firm—Wegner & Bretschneider

[57] ABSTRACT

Disclosed in this invention is a process for producing a long-chain dicarboxylic acid by culturing a fungus belonging to *Candida tropicalis* which has the ability to produce a long-chain dicarboxylic acid in a liquid medium containing a straight-chain saturated hydrocarbon as substrate, the production of said dicarboxylic acid being phenomenally increased by properly adjusting the pH of the medium in the course of culture. There is also disclosed a method for advantageously separating and collecting said dicarboxylic acid from a fermentation broth containing said dicarboxylic acid produced by said culture.

3 Claims, No Drawings

PROCESS FOR THE PREPARATION OF LONG-CHAIN DICARBOXYLIC ACIDS BY FERMENTATION

BACKGROUND OF THE INVENTION

This invention relates to an advantageous process for producing long-chain dicarboxylic acids from straight-chain hydrocarbons by utilizing the microorganisms as well as a method for separating and collecting the produced dicarboxylic acids.

Long-chain dicarboxylic acids are the useful material for the production of chemical products such as synthetic resin, aromatic, etc., and the demand for this material is on the increase. For these reasons, growing interest is shown lately for the method of producing such long-chain dicarboxylic acids according to a fermentation process by utilizing the microorganisms.

There has been proposed a method comprising culturing a fungus of the type capable of assimilating hydrocarbons, for example, a fungus belonging to *Candida tropicalis*, in a medium containing a straight-chain saturated hydrocarbon, particularly one having a carbon number of 11 to 18 as substrate, to thereby produce a long-chain dicarboxylic acid corresponding to said hydrocarbon (refer to M. Okuhara, Y. Kubochi and T. Harada, Agricultural & Biological Chemistry, Japan, Vol. 35, p. 1376(1971), Vol. 35, No. 13, p. 2033(1971) and Vol. 36, No. 3, p. 426(1972)).

However, in the heretofore proposed methods of producing long-chain dicarboxylic acids by means of fermentation techniques, including the above-said method, it is often experienced that various other germs contaminate the medium and grow in the medium in the course of culture of said type of fungus to impair the ability of said fungus, for the production of the dicarboxylic acid, resulting in very poor yield of the objective long-chain dicarboxylic acid.

Another problem in the course of the production of the long-chain dicarboxylic acid by fermentation is that great difficulties are accompanied at the steps of separation and collection of the objective long-chain dicarboxylic acid from the fermentation broth because various residual ingredients of the culture medium such as unreacted ingredients, water-soluble nutrient and eluate from the cultures exist in admixture with the objective long-chain dicarboxylic acid in the fermentation broth obtained from culture of the fungus. For example, when an extraction method is applied for separation and/or collection of the objective product, the unknown matters originating in said various substances existing in the fermentation broth are produced at the extraction interface in the fermentation broth, and such matters make it difficult to separate and collect the long-chain dicarboxylic acid from the fermentation broth.

This invention has been deviced with the object of solving the said problems in the conventional methods of producing long-chain dicarboxylic acids by use of fermentation techniques.

An object of this invention, therefore, is to provide a process for producing a desired long-chain dicarboxylic acid in a high yield without any impairment of the starting fungus by mixing and growth of other germs in the medium in the process of production of the objective long-chain dicarboxylic acid according to a fermentation method.

Another object of this invention is to provide a method whereby the long-chain dicarboxylic acid produced by using the fermentation techniques can be separated and collected from the fermentation broth in an advantageous way.

Other objects of this invention will become apparent from the following detailed description of the invention.

DETAILED DESCRIPTION OF THE INVENTION

A salient feature of this invention resides in that a fungus belonging to *Candida tropicalis* and capable of assimilating straight-chain hydrocarbons is used as the starting fungus for producing an objective long-chain dicarboxylic acid, and that the pH of the medium during the culturing operation is adjusted to 3.0 to 5.0 in the initial stage of culture and to 6.5 to 7.5 in the remaining process of culture.

Another feature of this invention is that an alkaline material is added to the fermentation broth containing a long-chain dicarboxylic acid produced from said culture to dissolve said dicarboxylic acid, then after further adding diatomaceous earth, said fermentation broth is filtered under pressure, and said dicarboxylic acid is precipitated from the obtained filtrate, the precipitated dicarboxylic acid being then separated and collected.

Still another feature of this invention resides in a process which comprises adding an alkaline material to the fermentation broth containing a long-chain dicarboxylic acid produced by said culture to dissolve said dicarboxylic acid, adding bleaching powder and/or a hypochlorite to prevent after-fermentation, further adding diatomaceous earth to said broth and filtering it under pressure, adjusting the pH of the obtained filtrate to 4 or below and heating it to a temperature above 50° C. to precipitate said dicarboxylic acid, and then separating and collecting said acid.

The microorganisms usable in this invention are those belonging to *Candida tropicalis* and having an ability to produce long-chain dicarboxylic acids from straight-chain hydrocarbons. They also include the so-called variants which are obtained by subjecting said microorganisms to a variation treatment such as X-ray irradiation or ultraviolet ray irradiation or by treating said microorganisms with a mutagen such as N-methyl-N'-nitrosoguanidine.

According to the process of this invention, a long-chain dicarboxylic acid producing fungus belonging to *Candida tropicalis* is inoculated into and cultured in a medium containing as substrate a straight-chain saturated hydrocarbon, particularly one having a carbon number of 11 to 18, by adjusting the pH of the medium within the range of 3.0 to 5.0 in the initial stage of culture and then within the range of 6.5 to 7.5 in the remaining course of culture, thereby producing in a high yield a long-chain dicarboxylic acid corresponding to the hydrocarbon used as substrate of the medium.

Other culturing conditions employed in this invention may be those usually used in the conventional methods. The medium composition used in this invention may be also one prepared in a known way, such composition containing a nitrogen source, inorganic salts, etc., of the commonly used type.

By performing culture of said dicarboxylic acid producing fungus in said medium by adjusting the pH of the medium to 3.0 to 5.0 in the initial stage of culture, it is possible to prevent impairment of the dicarboxylic acid producing ability of said fungus which may be caused by mixing and growth of other germs in the medium in the course of culture. The period in which the culture of said dicarboxylic acid producing fungus is to be performed by maintaining the medium pH at 3.0 to 5.0 is within the range of 6 to 24 hours, preferably about 12 hours, from start of culture.

In case of using saccharide such as sucrose, glucose, sorbitol, etc., as carbon source in the culturing stage of the seed culture of said dicarboxylic acid producing fungus, there takes place exuberant growth of the germs mixed in the medium in the initial stage of culture, so that it is desirable to perform culture by maintaining pH at 3.0 to 5.0 until said carbon source disappears.

As pH of the medium tends to drop with the progress of culture during said initial stage of culture, usually alkaline material such as NaOH or KOH is used as pH adjuster to control the pH value within the said range.

After completion of said initial stage of culture at pH 3.0–5.0, the culture is further continued by adjusting pH at 6.5–7.5.

The pH adjustment in said culture process is preferably made in the following procedure. The initial stage of culture is carried out in a medium supplied with a major portion of the total feed of the hydrocarbon used as substrate, and during this initial stage of culture, pH of the culture solution is maintained at 3.0 to 5.0 by using a part of the solution prepared by blending an alkaline material with the remaining portion of said hydrocarbon as pH adjuster, and then the culture is further continued by adjusting pH of the culture solution to 6.5 to 7.5 by using the remainder of said blended solution as pH adjuster. This procedure allows supplementary supply of hydrocarbon to the medium simultaneously with its pH adjustment, making it possible to advantageously produce the desired dicarboxylic acid by using a medium of a quantity corresponding to the capacity of the fermenter.

As means for addition of a hydrocarbon (as substrate) and alkaline material, they may be added simultaneously by previously mixing and forming them into an emulsion by a suitable method or they may be added separately from each other.

By thus varying the pH range of the medium in the culture process, it is possible to arrest growth of other germs to increase the yield of the objective dicarboxylic acid. Such variation of pH range can also control foaming of the culture solution in the initial stage of culture which often occurs in the conventional culture process, and this allows a reduction of the fermenter capacity and its effective utilization.

In this invention, an alkaline material such as caustic soda or caustic potash is added to the fermentation broth obtained by said culture to adjust pH of the solution to 10 to 13, preferably 11 to 12, to dissolve the dicarboxylic acid in said fermentation broth, and then diatomaceous earth is added. According to this treatment, the matters existing in admixture with the long-chain dicarboxylic acid in the fermentation broth, such as unreacted hydrocarbon, by-products such as mono-carboxylic acid, eluate from the culture, etc., are selectively adsorbed in diatomaceous earth, so that when said fermentation broth is filtered under pressure by using a filter press, there is obtained a filtrate in which the long-chain dicarboxylic acid substantially exists in the dissolved form.

Diatomaceous earth is used in an amount of 2–8% by weight based on said fermentation broth, and the type of diatomaceous earth used in this invention is preferably one which has a particle size within the range of 1–80μ. Said filtration is favorably performed under a pressure of 6–8 kg/cm$^2$, and the cake formed after this filtration is washed with 2 to 3 times as much amount of water and the obtained wash is mixed with said filtrate. In order to check after-fermentation, said fermentation broth is preferably adjusted to a pH of 11 to 12, and for more effectively preventing such after-fermentation, it is advised to add bleaching powder and/or a hypochlorite to the fermentation broth to which an alkali has been added to dissolve the long-chain dicarboxylic acid as said above. Such bleaching powder and/or a hypochlorite are added in such an amount that their content in the fermentation broth will be 20–200 ppm.

After adding bleaching powder and/or a hypochlorite to the fermentation broth to avoid after-fermentation, said broth is added with diatomaceous earth and filtered under pressure in the manner described above to obtain a filtrate containing a long-chain dicarboxylic acid.

The thus obtained filtrate is then added with a mineral acid such as sulfuric acid, whereby said dicarboxylic acid is precipitated, so the precipitate is further filtered thereby to separate and collect the long-chain dicarboxylic acid.

Precipitation of said dicarboxylic acid from said filtrate is preferably performed by controlling the pH of the filtrate at 4 or below, and the precipitation is preferably followed by heating to a temperature above 50° C. to grow the crystals.

If the pH of the filtrate is adjusted to 4 or below, there is eliminated the possibility that the dicarboxylic acid in the filtrate be brought into a "dissociated state" and solubility of said dicarboxylic acid in water is reduced to expedite precipitation thereof. Also, when the filtrate is maintained in said heated condition for a given period of time, there grow the crystals of the precipitated dicarboxylic acid to facilitate its separating operation by filtration.

Especially, in case that bleaching powder or a hypochlorite is added to the fermentation broth to avoid after-fermentation, it is necessary to decompose it by heating to thereby prevent the objective product from the contamination with the above material.

The bleaching powder or hypochlorite existed in the fermentation broth can be removed by heating said broth, in which the long-chain dicarboxylic acid has been precipitated, at a temperature above 50° C. for at least two hours, preferably 70°–80° C. for eight hours.

The thus precipitated long-chain dicarboxylic acid is filtered under pressure by using a filter press and the obtained cake is washed with water and dried. Effective drying can be accomplished when said cake is first granulated by an extrusion granulator and then dried by a hot air dryer.

Thus, according to this invention, a dicarboxylic acid with extremely high purity can be separated and collected in a high yield from a fermentation broth by adding diatomaceous earth to the fermentation broth containing a long-chain dicarboxylic acid, filtering said broth under pressure, and then precipitating said dicarboxylic acid from the filtrate under heating.

EXAMPLE 1

*Candida tropicalis* FERM-P No. 3,291 having the ability to produce a long-chain dicarboxylic acid from a straight-chain hydrocarbon was cultured in an incubator separately provided to obtain 120 liters of seed broth containing 10–15 g/l of cultured fungal body, and this seed broth was added into a reactor supplied with 1,200 liters of a medium containing 240 liters of n-tridecane.

This mixed solution was adjusted to pH 5 and cultured at 32° C. for 12 hours, during which period germ-free air was supplied at a rate of 400 l/min. Since the pH of the medium tends to drop during culture, a 10 N KOH solution was added to maintain said pH at 5.0±0.1. After this 12-hour culture, the pH of the medium was shifted to 7.0 and culture was further continued for additional 72 hours.

After this 72-hour culture, there was obtained 1,200 liters of fermentation broth containing 40 g/l of brassylic acid (1,11-undecanedicarboxylic acid), 8 g/l of n-tridecane and 20 g/l of cultured fungal body.

The population of other germs in the fermentation broth was less than 10 cell/ml.

Comparative Example 1

120 liters of seed broth prepared in the same way as described in Example 1 was added into a reactor provided with 1,200 liters of a medium containing 240 liters of n-tridecane, and the mixed solution was subjected to 84-hour culture at 32° C. and pH 7.0 under otherwise same conditions as Example 1. The obtained fermentation broth contained 15 g/l of brassylic acid, 40 g/l of n-tridecane and 13 g/l of cultured fungal body.

Existence of other germs than the fungus having the brassylic acid producing ability was found in a population of $10^9$ cell/ml in the fermentation broth.

In this method, there took place foaming in the medium and incidental effluence of a part of the medium along with the blown air, resulting in approximately 10% loss of the medium after 84-hour culture.

EXAMPLE 2

1,200 liters of a medium containing 80 liters of n-tridecane was supplied into a fermenter, and after sterilization at 122° C. for 30 minutes, 120 liters of seed broth containing 10–15 g/l of cultured fungal body, prepared in the same procedure as described in Example 1, was added into said fermenter. The pH of this culture medium was adjusted to 3.0 and culture was continued at 32° C. for 8 hours. Because of possible drop of the medium pH during this culture period, 10 N KOH was added to the medium to maintain its pH at 3.0±0.1.

N-tridecane of an amount three times that of KOH used for said pH adjustment was also simultaneously added into said fermenter.

Culture was performed at the condition of pH 3.0±0.1 of the medium as said above for 8 hours, and then the medium pH was shifted to 7.3 and culture was further continued at 32° C. for 76 hours. N-tridecane was supplied together with an alkaline matter for said pH adjustment, too.

There was obtained 1,150 liters of fermentation broth containing 45 g/l of brassylic acid, 1 g/l of n-tridecane and 20 g/l of cultured fungal body.

EXAMPLE 3

This example shows a method of separating and collecting a long-chain dicarboxylic acid from fermentation broth containing said dicarboxylic acid.

Culture was carried out by following the procedure of Example 1 to obtain 1.4 m³ of fermentation broth (pH: 7.25) containing 40 kg/m³ of brassylic acid, 1 kg/m³ of tridecanoic acid, 10 kg/m³ of n-tridecane and 20 kg/m³ of cultured fungal body. This fermentation broth was added with 12.5 N KOH to adjust its pH to 11.0 and then added with 40 kg of diatomaceous earth and agitated. The mixture was then filtered by a filter press. Filtering pressure was maintained at 6 to 8 kg/cm² to keep the moisture content in the cake below 80 wt% on dry base.

After filtration, the cake was washed with approximately thrice as much amount of water and the obtained liquid was added to the filtrate. This mixed solution was added with concentrated sulfuric acid to reduce its pH to 4 to thereby separate brassylic acid. The precipitate was heated to 80° C. under agitation and maintained at this temperature for 8 hours to grow the crystal grains, followed by filtration by a filter press under pressure of 8 kg/cm². The cake was washed with about thrice as much amount of water. The water content of this cake was 80 wt % on dry base. This cake was granulated by an extrusion granulator to form the particles with sizes of 10–15 mm $\phi \times 20$ to 30 mm and these particles were treated by a hot air dryer (at 75° C. for 3 hours) to obtain white brassylic acid.

There was obtained 56 kg of white brassylic acid with purity (as measured by gas chromatograhy) of as high as 97%. Said brassylic acid contained 2.0 wt % of methanol insolubles. No tridecanoic acid was detected in the product by gas chromatography.

The cultured fungus cake containing diatomaceous earth obtained from said filtration contains nitrogen, phosphoric acid and potassium and has incompressibility which is a powder characteristic of diatomaceous earth, so that it has excellent water and air permeability and can be used as fertilizer having a soil conditioning effect.

Referential Example 1

It was attempted to separate the fermentation broth obtained after the manner of Example 3 by using a centrifugal separator, but it was unable to effectively separate the solid matter.

EXAMPLE 4

1.4 m³ of fermentation broth (pH: 7.25) containing 42 kg/m³ of dodecanedioic acid (1,10-decamethylenedicarboxylic acid), 0.9 kg/m³ of dodecanoic acid, 11 kg/m³ of n-dodecanoic acid and 22 kg/m³ of cultured fungal body was obtained from culture conducted in the same way as Example 1 except for use of a medium containing n-dodecane as substrate, and this fermentation broth was added with 50 ppm of bleaching powder, stirred, then exposed to the atmosphere and left under this condition for 5 days. This broth was then added with 12.5 N KOH to adjust its pH to 11.0 and treated by following the procedure of Example 3 to obtain dodecanedioic acid in the form of white solid.

The obtained solid weight was 58 kg, and the purity of dodecanedioic acid as measured by gas chromatography was 96.5%.

No dodecanoic acid was detected by gas chromatography.

EXAMPLE 5

The fermentation broth same as used in Example 4 but not added with bleaching powder was exposed to the atmosphere and left under this condition for 5 days, recovering the white solids of dodecanedioic acid by following the same procedure as used in Example 4.

The fermentation broth was treated under the same condition as used in Example 3 except that 80 kg of diatomaceous earth was added.

The obtained white solid weight was 50 kg, and the purity of dodecanedioic acid as measured by gas chromatography was 95%.

No dodecanoic acid was detected by gas chromatography.

What is claimed is:

1. A process for producing a long-chain dicarboxylic acid which comprises culturing a fungus belonging to *Candida tropicalis* capable of assimilating straight-chain hydrocarbons in a liquid medium containing a straight-chain hydrocarbon as a substrate to obtain a fermentation broth containing a long-chain dicarboxylic acid corresponding to said hydrocarbon, dissolving said dicarboxylic acid in the fermentation broth by adding an alkaline material to said broth, further adding diatomaceous earth to said fermentation broth, filtering it under pressure, precipitating the long-chain dicarboxylic acid in the thus obtained filtrate by heating said filtrate to a temperature above 50° C. while adjusting the pH value of the filtrate to 4 or below by adding a mineral acid to the filtrate, and then separating and collecting the precipitated long-chain dicarboxylic acid.

2. The process according to claim 1, wherein the pH value of the medium is within the range of 3.0 to 5.0 in the initial stage of culturing and then within the range of 6.5 to 7.5 in the succeeding state of culturing.

3. The process according to claim 1 or 2, wherein bleaching powder and/or a hypochlorite are added to the fermentation broth before addition of diatomaceous earth.

* * * * *